US011600396B2

(12) United States Patent
Pal et al.

(10) Patent No.: US 11,600,396 B2
(45) Date of Patent: Mar. 7, 2023

(54) SYSTEMS AND METHODS FOR COLLECTING LOCATION AGNOSTIC CLINICAL AND NON CLINICAL DATA

(71) Applicant: CliniOps, Inc., Fremont, CA (US)

(72) Inventors: Avik. Kumar Pal, Fremont, CA (US); Yerramalli Subramaniam, Pleasanton, CA (US)

(73) Assignee: CliniOps, Inc., Fremont, CA (US)

( * ) Notice: Subject to any disclaimer, the term of this patent is extended or adjusted under 35 U.S.C. 154(b) by 304 days.

(21) Appl. No.: 16/862,505

(22) Filed: Apr. 29, 2020

(65) Prior Publication Data

US 2021/0343428 A1    Nov. 4, 2021

(51) Int. Cl.
*G16H 80/00* (2018.01)
*H04L 9/40* (2022.01)
*G16H 10/60* (2018.01)

(52) U.S. Cl.
CPC .............. *G16H 80/00* (2018.01); *G16H 10/60* (2018.01); *H04L 63/166* (2013.01)

(58) Field of Classification Search
CPC ........ G16H 10/20; G16H 80/00; G16H 20/30; G16H 40/63; G16H 40/67
USPC .......................................................... 705/2
See application file for complete search history.

(56) References Cited

U.S. PATENT DOCUMENTS

2013/0262357 A1* 10/2013 Amarasingham ...... G16H 50/70
706/21
2015/0213202 A1* 7/2015 Amarasingham ...... G16H 50/50
705/2

FOREIGN PATENT DOCUMENTS

WO    WO-2017070255 A1 *  4/2017  ........... G06F 16/248

OTHER PUBLICATIONS

Ryan, Lynne Garez; Prevalence of Dissociative Disorders and Symptoms in a University Population; California Institute of Integral Studies. ProQuest Dissertations Publishing, 1988. 8908898. (Year: 1988).*
Hagen, Ryan; The Use of Passive Smartphone Data in the Assessment of Mood; William James College, ProQuest Dissertations Publishing, 2013. 10184556. (Year: 2013).*

* cited by examiner

*Primary Examiner* — Hiep V Nguyen
(74) *Attorney, Agent, or Firm* — Shumaker, Loop & Kendrick, LLP (57) ABSTRACT

Systems and methods for collecting clinical trial data across multiple locations is described. One described method; decentralized clinical trial design; comprises collecting clinical and non-clinical data on a client device over a network; the data is collected at a hospital, home or an alternate care facility, by either the patient or the healthcare professional; and transmitting the data, for access to sponsors over the network.

7 Claims, 8 Drawing Sheets

SYSTEMS AND METHODS FOR COLLECTING LOCATION AGNOSTIC CLINICAL AND NON CLINICAL DATA

FIELD OF THE INVENTION

The present invention relates generally to clinical trial data collection. This invention more particularly relates to the collection of the clinical trial data across multiple locations.

BACKGROUND

Historically, clinical trials have always been designed where patient data is collected at the trial sites (hospitals, health centers). Patients would visit these sites at per a pre-defined schedule (known as visit calendar) for the duration of the study.

There are several challenges to this mode of patient data collection. Usually patients have to commute for about 2 hrs on an average, and the process is not very convenient for the patients. Apart from the commute there is also a significant wait times at multiple touch points between front desk, nurse, doctors etc. Sometimes a visit can cost a patient a full day with all the commute and wait times. If the patient is a student, then he/she will most probably miss school, and the parent will miss out from work. All these challenges and more, usually leads to a lot of patient drop-outs over time making it very difficult to retain a patient throughout the duration of the trial which can last anywhere between 6 months to 3 years or more.

There is also a lot of cost burden from the sponsor's end, to pay for the hospital facility, the overheads and the multiple touch points, making running clinical trials in the traditional mode a significantly costly affair, in addition to providing monitory incentives to the patients to continue on the trial till the end. The sponsors are any organization sponsoring the clinical trial which can be Pharma companies, Biotech companies, Med device companies or the like.

Over the years, technology has evolved multi-fold and so did the adoption of technology by patients, nurses, doctors, care givers and other stake holders involved in the process. As more and more millennials come into the mix as doctors, nurses or patients, the adoption curve of technology is only expected to increase.

Many of the visits that patients are currently commuting to hospitals, can now be done from the convenience of their home, by leveraging technology, like telemedicine or other forms of remote communication between the patient and the care team. This mode of communication is not only very convenient for the patients but also is much more cost effective for the sponsors and sites to significantly reduce the cost burden of running the clinical trial.

There is a need to rethink the systems and methods needed to support this alternate process of patient doctor interaction and collection of location agnostic clinical trial data.

SUMMARY

Embodiments of the present invention provide systems and methods for collecting clinical trial data across multiple locations. In one embodiment of the present invention, a method comprises collecting clinical and non-clinical data on a client device over a network; the data is collected at a hospital, home or an alternate care facility, by either the patient or the healthcare professional; and transmitting the data, for access to sponsors over the network.

This embodiment is illustrative and is an example to help with the understanding thereof. Illustrative embodiments are discussed in the Detailed Description section.

FIGURES

The benefits, needs and advantages of this current invention is better understood, when the following Detailed Description below is read with reference to the drawings in this section, wherein.

DETAILED DESCRIPTION

Embodiments of the present invention comprise systems and methods to collect clinical and non-clinical trial data across multiple locations.

First recorded clinical trials was done in 1946. Since then the industry has come a very long way but things have not changed much since mid 1990s. But now the industry is at a point of inflexion and one of the area which is very promising is the decentralized clinical trial (DCT). Over the last few years technology has also evolved in leaps and bounds to support patient data collection from the convenience of their home. Apart of the burden of having the patients come of the hospitals for every visit, a decentralized solution supporting patient data collection from home can also significantly bring down the cost pressure on the sponsors of running such trials.

The industry needs a solution that would delve deeper into and analyze the issues of source data generation across location (hospital, home, alternate care facility), and user types (patient, healthcare professional, nurse, doctor, care team member or sponsor study team member) and minimize data verification, through technology innovations, thereby bringing drugs faster to market at a much reduced cost.

With FDA pro-actively developing guidelines supporting the use of technology in decentralized trials, the onus is on the clinical trial industry to adopt innovative solutions, that will not only reduce the time and cost for Pharma and CROs but also drastically improve the data quality, reduce patient burden and patient attrition, which is one of the most challenging problems that the industry is currently facing. The current systems are fragmented resulting in many gaps & unmet needs in the industry. CliniOps's innovative DCT solution leverages cutting-edge technologies such as Social, Mobile, Analytics & Cloud (SMAC) to drastically transforms the way decentralized clinical trials can be conducted reducing the time & cost of collecting data while simultaneously improving its quality. With real-time data from any location or any user type, real-time decision support solutions leveraging AI/ML technologies can also be developed.

CliniOps approach in the concept of decentralized trials is to promote more data collection from patient homes, and enable the patients with simple tool and technology to ensure seamless data collection from home possible. Hence the approach here is to design a future proof solution that provides the tools and processes to meet current needs as well as gradually transition into decentralized trials.

CliniOps envisions a holistic, digitalized & automated solution for decentralized clinical trials that will seamlessly capture subject data electronically at point-of-care and provide a globally accredited Clinical Data Interchange Standards Consortium (CDISC) compliant dataset, and satisfies all regulatory requirements. CliniOps's user-friendly interface ensures end-user acceptance and the product's built-in design with extremely streamlined workflow eliminates manual data collection points, costly and often challenging system integrations, saves time & money by drastically curbing duplication & redundant efforts.

Figure 1:
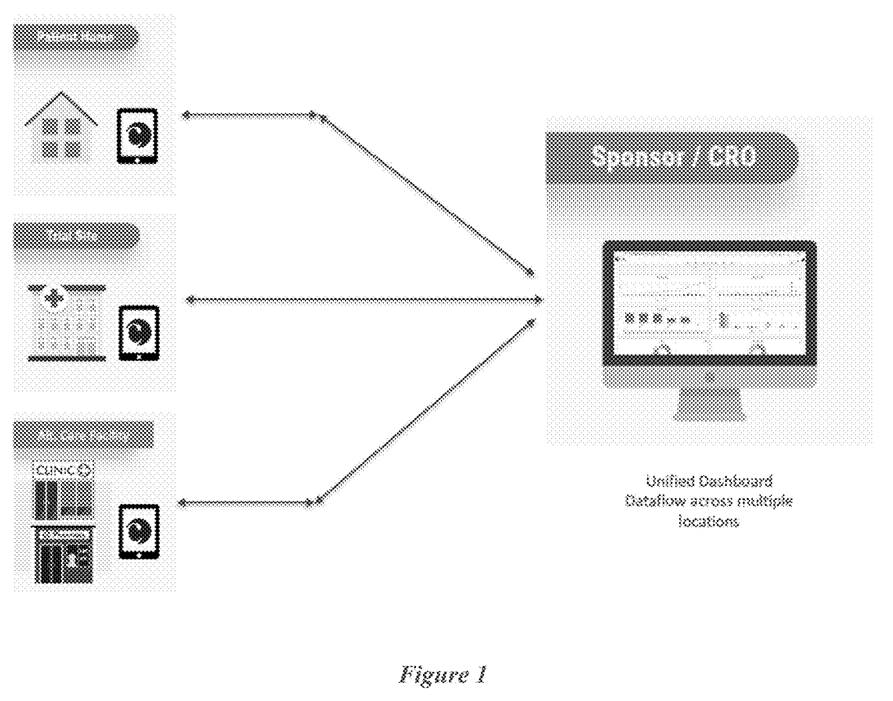
FIG. 1 is a schematic illustrating of the functional design, in one embodiment of the present invention of decentralized trial design, to collect data from home, hospital or alternate care facility, supported with a unified dashboard across multiple locations.

FIG. 1 is a schematic illustrating of the functional architecture, in one embodiment of the present invention of decentralized trial design, to collect data from hospital, home or alternate care facility, by a healthcare professional or patient, supported through a single portal. As the decentralized clinical trial adoption is increasing there are multiple ways that data can be collected. The current embodiment includes:
 a client device; and
 a collection of clinical and non-clinical data; and
 wherein the said clinical and said non-clinical data on the said client device is collected at a hospital location; and
 wherein the said clinical and said non-clinical data on the said client device is collected at a home location; and
 wherein the said clinical and said non-clinical data on the said client device is collected at an alternate care facility location; and
 wherein the said clinical and said non-clinical data on the said client device at the said hospital location can be collected by a healthcare professional; and
 wherein the said clinical and said non-clinical data on the said client device at the said hospital location can be collected by a patient; and
 wherein the said clinical and said non-clinical data on the said client device at the said home location can be collected by the said healthcare professional; and
 wherein the said clinical and said non-clinical data on the said client device at the said home location can be collected by the said patient; and
 wherein the said clinical and said non-clinical data on the said client device at the said alternate care facility location can be collected by the said healthcare professional; and
 wherein the said clinical and said non-clinical data on the said client device at the said alternate care facility location can be collected by the said patient; and
 wherein transmitting the said clinical and said non-clinical data collected at the said locations, to the server over the network, for access to sponsors.

The challenge is to have a technology solution to support all these data collection modalities in a compliant way and have all these data centrally available in a single dashboard in real-time, for review, analysis, and prompt action as needed. Existing technological solutions are currently designed to cater to a few of the above options. There are manual and legacy processes to cater to some of the other modes of data collection. The proposed invention here is architected in such a way that irrespective of the user type and location, all data can be seamless collected and transmitted to the central hub for review and analytics.

Figure 2:
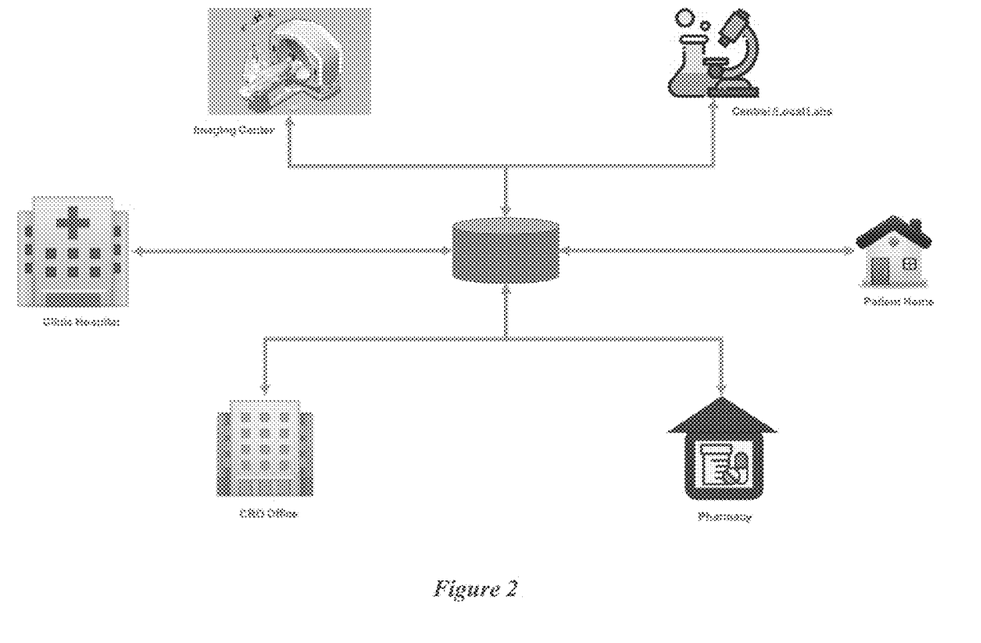
FIG. 2 is a schematic illustrating of the system design, in one embodiment of the present invention of decentralized trial design, to collect data from various sources (home devices, hospital systems, lab equipment etc), collected through various secured protocols.

FIG. 2 is a schematic illustrating of the system overview, in one embodiment of the present invention, to collect data from various sources and locations. Patient usually visits the clinic or hospital only for the first visit and then stays home for the most part of the study duration. In this case the baseline data is collected at the hospital and for subsequent visits the patient can collect and send the data from home. The bio specimen are also collected directly from patients home and sent to the central lab. The central lab analyzes those samples and the data is automatically uploaded to the central repository. Similarly if any imaging has to be collected for the study, patient can visit the nearest imaging center and subsequently the imaging data is also uploaded to the central repository. The data managers and data monitors at CRO location can monitor all the data remotely. Care providers can also look at the data remotely and proactively connect with the patient if any intervention is warranted.

Figure 3:
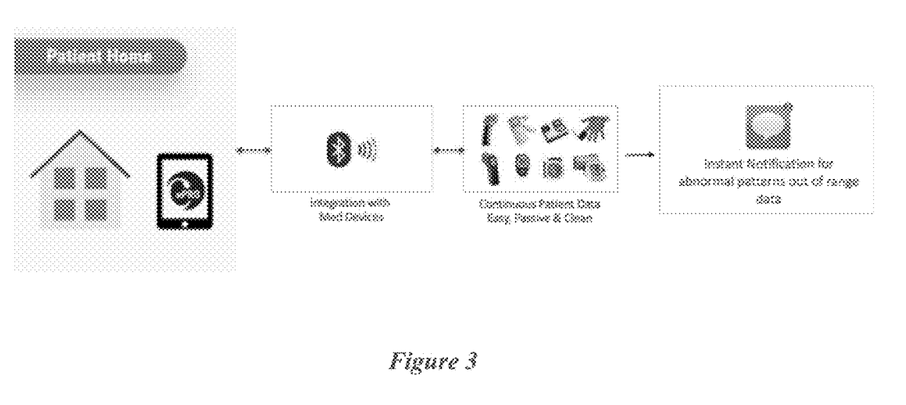
FIG. 3 is a schematic illustrating of the functional design, in one embodiment of the present invention of decentralized trial design, that extends data collection at home, via bluetooth integration with medical devices.

FIG. 3 is a schematic illustrating of the functional architecture, in one embodiment of the present invention, that enables data collection at home, via smartphone and medical devices. Currently, only a small subset of clinical trials are designed to support data collection from home, but as more and more homes becomes Smarthomes with IoT and connected devices, the process of patient data collection from home will become more and more mainstream. The invention here is capable to collect data from connected devices at home using wired, wireless, or through bluetooth connections. The system also supports automatic notification to sites and sponsors if any high-risk data is detected by the system, thereby enabling prompt action as needed.

Figure 4:
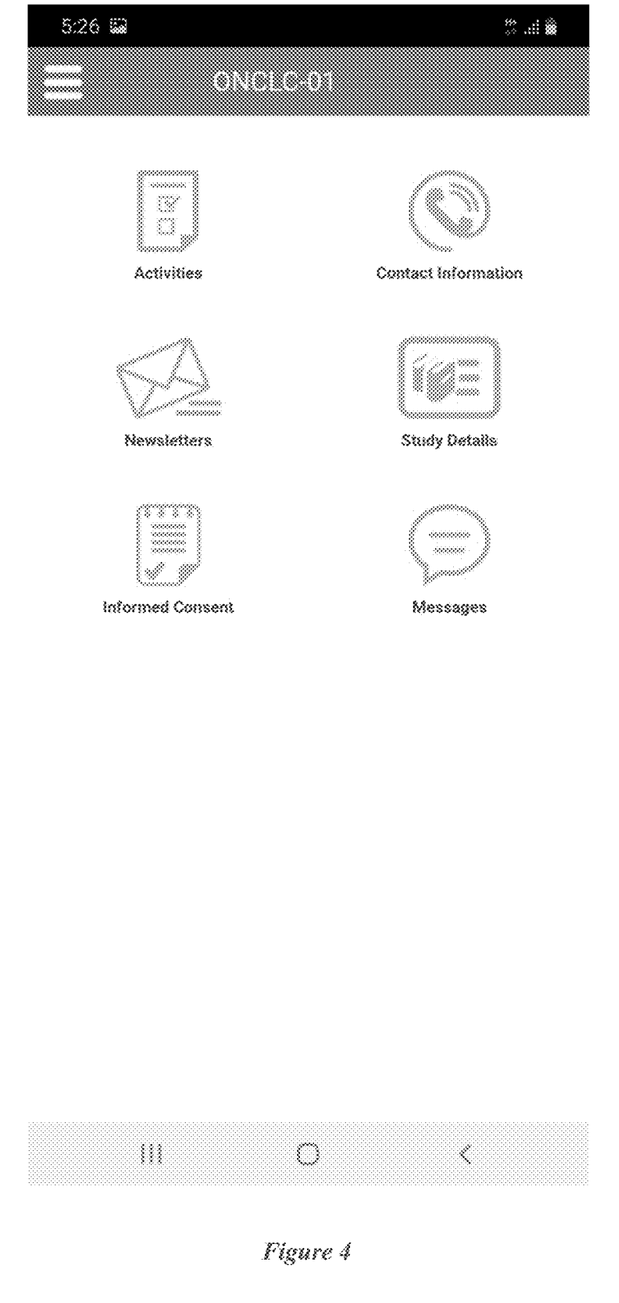
FIG. 4 is a screenshot of the mobile application, in one embodiment of the present invention, that provides site details, newsletters, contact information from within the mobile application

FIG. 4 is a screenshot of the mobile application, in one embodiment of the present invention, that provides site details, newsletters, Contact information from within the system. These information keeps the patient engaged and informed at all times resulting in better care and improvement in protocol adherence by the patients. These can also be used to provide details of each visits and what to expect when they visit hospital or clinic for a scheduled visit.

Figure 5:
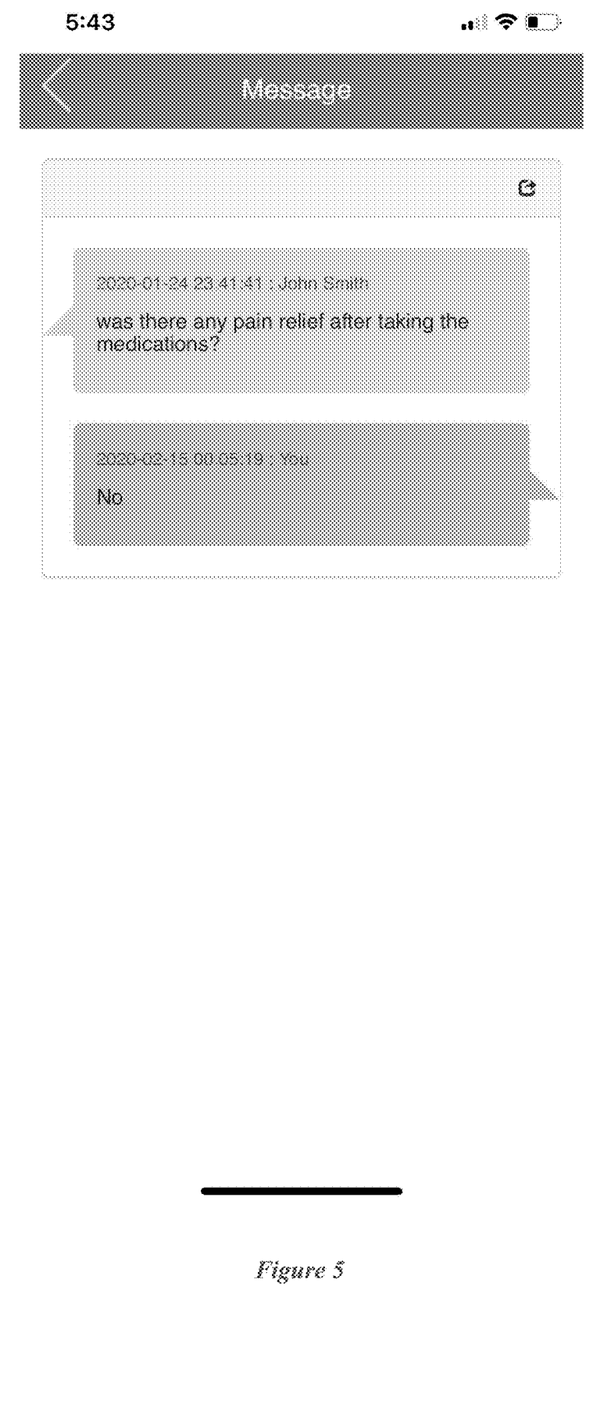
FIG. 5 is a screenshot of the mobile application, in one embodiment of the present invention, that provides patient doctor interaction functionality, from within the mobile application

FIG. 5 is a screenshot of the Mobile application, in one embodiment of the present invention, that provides patient-doctor interaction functionality, from within the system. As trials become more and more decentralized, it's important to ensure that the patients and doctors constantly stay in touch and any challenges due to location barriers are minimized.

This constant interaction between the patient and doctor also increases patient engagement and improves protocol adherence by the patients.

Figure 6:
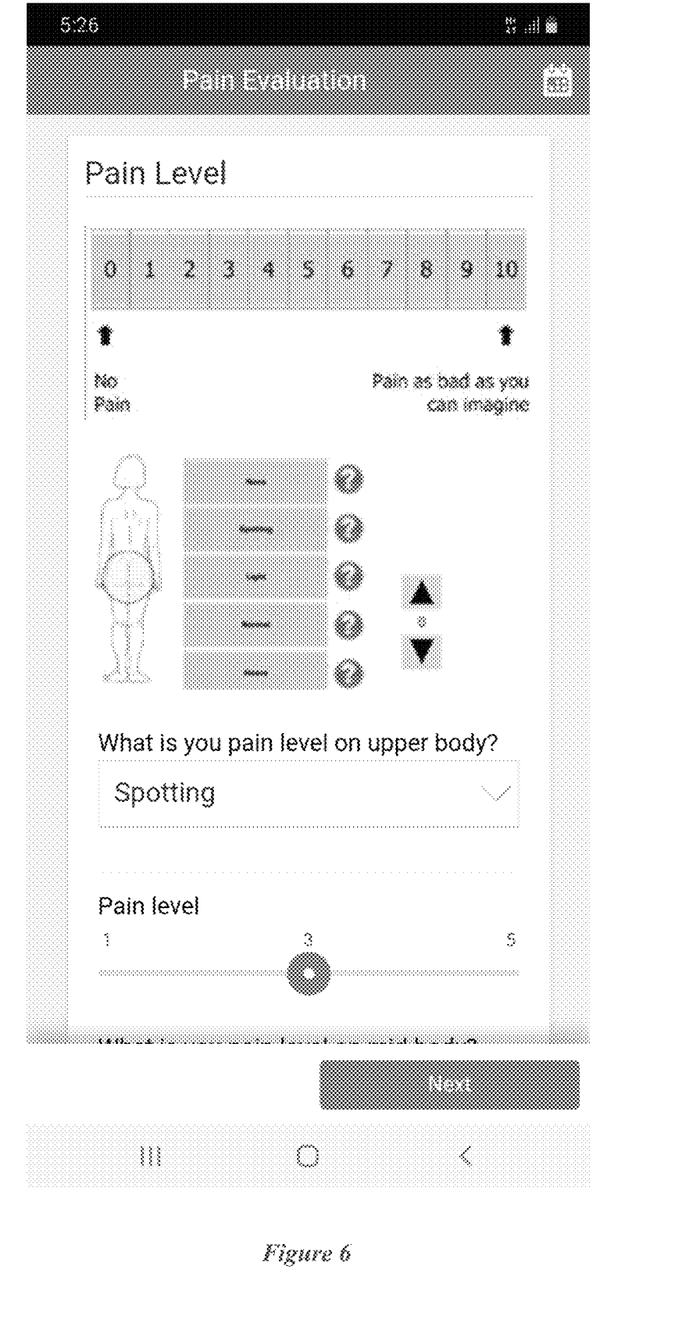
FIG. 6 is a screenshot of the mobile application, in one embodiment of the present invention, that identifies patient pain level from within the mobile application

FIG. 6 is a screenshot of the mobile application, in one embodiment of the present invention, that identifies patient pain level from within the system. Since the patients are expected to collect their own data, it's important to ensure that the process of data collection is made very simple and easy to use by the patients. The solution supports graphical images to easily spot pain areas and supports simple gestures and other mobile touch screen technologies for example slider to ensure the process is seamless. As more and more millennials enter the clinical trial industry both as patients and/or doctors, the dependence on cutting technology is only going to increase.

Figure 7:
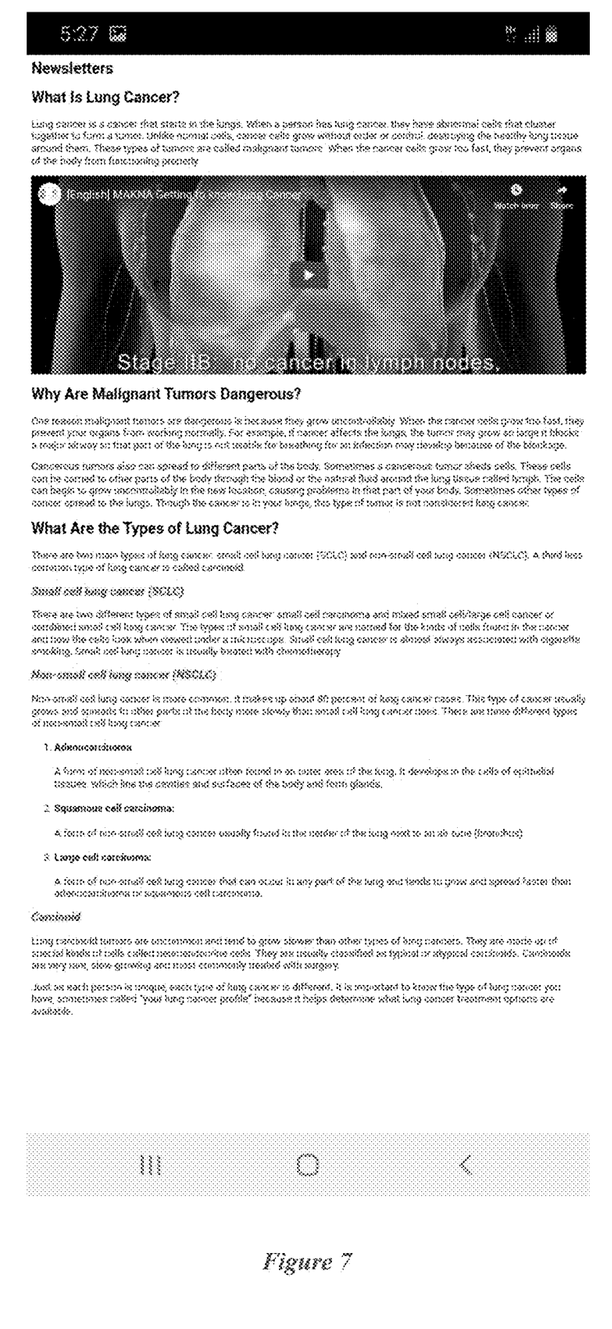
FIG. 7 is a screenshot of the mobile application, in one embodiment of the present invention, that provides newsletters and study specific details to promote patient engagement, from within the mobile application

FIG. 7 is a screenshot of the Mobile application, in one embodiment of the present invention, that provides newsletters and study specific details to promote patient engagement, from within the solution. The ability to provide regular newsletters, education materials, videos and other information ensures that patients are constantly kept informed by the sites. As these digital communication modes increases, it will automatically reduce the in-person touchpoints to a minimal, saving time and costs for all and increase patient convenience.

Figure 8:
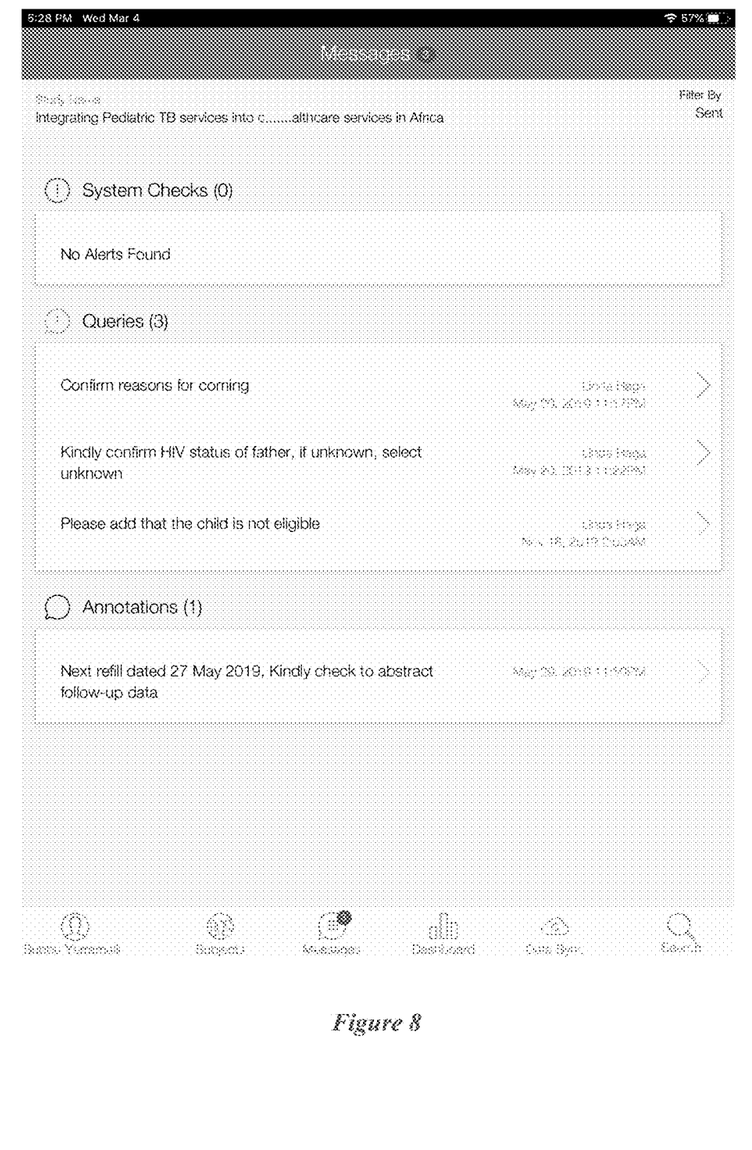
FIG. 8 is a screenshot of the mobile application at the site (hospital), in one embodiment of the present invention, that provides seamless sponsor-site communication, from within the mobile application

FIG. 8 is a screenshot of the mobile application at the hospital, in one embodiment of the present invention, that provides seamless sponsor-site communication, from within the system. The study portal is designed in a very collaborative way to provide role-based access to various user types across sites, sponsors and patients. The sponsors can also look at patient data in real-time and communicate with sites for any abnormalities in the data collected, or provide site specific information as needed from within the system. These communications can originate through the portal on the sponsor's end, and is designed to show up on the digital tablets used by the site users.

One embodiment provides access to the entire dataset of all patient records during and after a study. Access to historical data after completion of the trial may include downloading a PDF of the entire chart for a selected subject or selected subjects.

Decentralized trials are definitely the future but the entire clinical ecosystem needs to be designed carefully to support that. Large Bio-Pharma companies are already running pilots and feasibility studies, but hopefully they will soon become mainstream due to its several benefits including cost, time and patient convenience.

Some embodiments of the present invention are compliant with some or all of both HIPAA and FDA 21 CFR Part 11 regulations. FDA 21 CFR Part 11 covers all aspects of electronic records including signatures, integrity and authenticity, record creation, audit trails and archiving of data. Part 11 requires electronic records that are "created, modified, maintained, archived, retrieved, or transmitted, under any records requirement set forth in agency regulations" may be protected by procedures and controls to "ensure the authenticity, integrity, and, when appropriate, the confidentiality of electronic records, and to ensure that the signer cannot readily repudiate the document as not genuine." The goal of Part 11 is to ensure electronic records and signatures are authentic and traceable. Without the rule, accidental or deliberate tampering with electronic patient records would be difficult to monitor.

The above description of the embodiments of the invention has been presented for the purpose of illustration and description and is not intended to be exhaustive or to limit the invention to the precise apps disclosed. Modifications and additional features and capabilities thereof may be apparent, without departing from the spirit and scope of the present invention.

That what is claimed:

1. A method implemented by a system for smart data collection of a decentralized clinical trial (DCT), wherein the method comprises:

collecting, by a processor, clinical trial data and non-clinical trial data, from a device associated with a first set of users at a first location, and wherein the device is a wired device, a wireless device, or a Bluetooth device, and wherein the first location is a hospital, a home, or an alternate care facility, and wherein the first set of users comprises a healthcare professional or a patient, and wherein the clinical trial data is data collected for a decentralized clinical trial for a clinical research, a patient care, and wherein the clinical trial data comprises at least a bio-specimen data, an imaging data, a lab analysis data, and wherein the non-clinical trial data comprises a historical data, a contact information, and a patient-doctor interaction data;

displaying, by the processor, a user selectable graphic element representing a level of pain on a user interface on the device, wherein the level of pain is denoted on a graphical scale comprising a range of the level of pain on the user selectable graphic element, and wherein the range starts with a minimum level of pain and ends with a maximum level of pain;

receiving, by the processor, at least one of the clinical trial data through a user selection of the level of pain on the graphical scale within the range displayed on the user graphic element, wherein the level of pain is received by the user selection using a slider to select the level of pain on the user graphical element on the user interface;

transmitting, by the processor, the clinical trial data and the non-clinical trial data collected at the first location to a central hub;

automatically converting, by the processor, the clinical trial data and the non-clinical trial data to a compliant dataset, wherein the compliant dataset complies with a regulatory standard for the clinical trial data;

configuring, by the processor, a role-based access to the compliant dataset to a second set of users, wherein the second set of users comprises a sponsor, a data manager, a care provider, the patient, and the healthcare professional;

providing, by the processor, the compliant dataset with the role-based access in real time to the second set of users;

facilitating, by the processor, a real time decision making by the second set of users, wherein the sponsor is given real time access to the compliant dataset for decision making and analytics in real time;

detecting, by the processor, a high-risk data, wherein the high-risk data necessitates a prompt action; and automatically notifying, by the processor, at least one user of the second set of users upon detecting the high-risk data, thereby enabling further data collection for a decentralized clinical trial.

2. The method as claimed in claim 1, further comprising:

remotely monitoring, by the processor, the clinical trial data, the non-clinical trial data and the compliant dataset by the data manager and the care provider;

providing, by the processor, a regular newsletter and the clinical trial data to the patient, wherein the clinical trial data corresponds to the patient;

connecting, by the processor, the patient, the healthcare professional, and the sponsor through a central hub, wherein the sponsor and the patient communicate in real time;

automatically maintaining, by the processor, an electronic record of the clinical trial data, the non-clinical trial data, and the compliant data set, wherein the maintenance comprises a signing, an archiving, a retrieval, an audit, and a transmittal of the electronic record; and maintaining, by the processor, an authenticity, an integrity, and a confidentiality of the electronic record.

3. The method as claimed in claim 1, wherein the clinical trial data is collected as one of a biospecimen, an image and a graphical image, and wherein the image is a scanned image or an x-ray image.

4. The method as claimed in claim 1, wherein the decision making and analytics in real time is based on artificial intelligence and machine learning.

5. The method as claimed in claim 1, wherein the clinical trial data and the non-clinical trial data is collected from the device, at the location, and via an integration with a medical device.

6. A system for smart data collection of a decentralized clinical trial (DCT), the system comprising:
   a memory;
   a processor coupled to the memory, wherein the processor is configured to execute a set of instructions stored in the memory to:
      collect a clinical trial data and a non-clinical trial data, from a device associated with a first set of users at a first location, and wherein the device is a wired device, a wireless device, or a Bluetooth device, and wherein the first location is a hospital, a home, or an alternate care facility, and wherein the first set of users comprises a healthcare professional or a patient, and wherein the clinical trial data is data collected for a decentralized clinical trial for a clinical research, a patient care, and wherein the clinical trial data comprises at least a bio-specimen data, an imaging data, a lab analysis data, and wherein the non-clinical trial data comprises a historical data, a contact information, and a patient-doctor interaction data;
      display a user selectable graphic element representing a level of pain on a user interface on the device, wherein the level of pain is denoted on a graphical scale comprising a range of the level of pain on the user selectable graphic element, and wherein the range starts with a minimum level of pain and ends with a maximum level of pain:
      receive at least one of the clinical trial data through a user selection of the level of pain on the graphical scale within the range displayed on the user graphic element, wherein the level of pain is received by the user selection using a slider to select the level of pain on the user graphical element on the user interface;
      transmit the clinical trial data and the non-clinical trial data collected at the first location to a central hub;
      automatically convert the clinical trial data and the non-clinical trial data to a compliant dataset, wherein the compliant dataset complies with a pre-defined regulatory standard for the clinical trial data;
      configure a role-based access to the compliant dataset to a second set of users, wherein the second set of users comprises a sponsor, a data manager, a care provider, the patient, and the healthcare professional;
      provide the compliant dataset with the role-based access in real time to the second set of users;
      facilitate real time decision making by the second set of users, wherein the sponsor is given real time access to the compliant dataset for decision making and analytics in real time;
      detect a high-risk data, wherein the high-risk data necessitates a prompt action; and
      automatically notify at least one user of first set of users upon detecting the high-risk data to the one or more users upon detection of the high-risk data, thereby enabling further data collection for a decentralized clinical trial.

7. The system as claimed in claim 6, further configured to:
   remotely monitor the clinical trial data, the non-clinical trial data and the compliant dataset by the data manager and the care provider;
   provide a regular newsletter and the clinical trial data to the patient, wherein the clinical trial data corresponds to the patient;
   connect the patient, the healthcare professional and the sponsor through a central hub, wherein the sponsor and the patient communicate in real time;
   automatically maintain an electric record of the clinical trial data, the non-clinical trial data, and the compliant data set, wherein the maintenance comprises a signing, an archiving, a retrieval, an audit, and a transmittal of the electronic record; and
   maintain an authenticity, an integrity, and a confidentiality of the electronic record.

\* \* \* \* \*